United States Patent [19]

Hess et al.

[11] Patent Number: 5,411,037
[45] Date of Patent: May 2, 1995

[54] ELASTIC KNEE-JOINT BANDAGE

[75] Inventors: Heinrich Hess, Saarlouis; Wolfgang Krause, Kassel; Hans B. Bauerfeind, Kempen, all of Germany

[73] Assignee: Bauerfeind GmbH & Co., Kempen, Germany

[21] Appl. No.: 81,852

[22] PCT Filed: Nov. 14, 1989

[86] PCT No.: PCT/DE89/00713

§ 371 Date: Jul. 20, 1990

§ 102(e) Date: Jul. 20, 1990

[87] PCT Pub. No.: WO90/05510

PCT Pub. Date: May 31, 1990

Related U.S. Application Data

[63] Continuation of Ser. No. 536,618, Jul. 20, 1990, abandoned.

[30] Foreign Application Priority Data

Nov. 14, 1988 [DE] Germany .................. 38 38 576.7

[51] Int. Cl.[6] ........................... A61F 5/37; A61F 5/00
[52] U.S. Cl. .................................. 128/882; 602/23; 602/26; 602/62; 602/63
[58] Field of Search ................ 602/23, 26, 62, 63; 128/882

[56] References Cited

U.S. PATENT DOCUMENTS

| | | | |
|---|---|---|---|
| 3,074,400 | 1/1963 | Schulman | 128/80 C |
| 3,084,685 | 4/1963 | Lewis | 128/80 C |
| 3,375,821 | 4/1968 | Meek | 128/80 R |
| 4,116,236 | 9/1978 | Albert | 128/80 C |
| 4,201,203 | 5/1980 | Applegate | 128/80 C |
| 4,287,885 | 9/1981 | Applegate | 128/80 C |
| 4,353,362 | 10/1982 | DeMarco | 128/80 C |
| 4,607,628 | 8/1986 | Dashefsky | 128/80 C |
| 4,651,722 | 3/1987 | Karczewski | 128/80 C |
| 4,700,698 | 10/1987 | Kleylein | 128/80 C |

Primary Examiner—Michael A. Brown

[57] ABSTRACT

An elastic knee joint bandage is in tubular form with an elastic profile insert encircling the knee cap in an opening. The areas of the profile insert adjacent to the poles of the knee cap are connected by a flexible, unstretchable tension member placed around the knee cap in a curve in the profile insert on the side of the fibula, so that when the distance between these areas is increased by flexing the knee joint, the distance of the curve from the line joining the poles of the knee cap is reduced, and the edge of the opening of the profiled insert in question on the adjacent side of the knee cap presses it medially with a shifting and centering effect.

6 Claims, 4 Drawing Sheets

ELASTIC KNEE-JOINT BANDAGE

This is a continuation of application Ser. No. 07/536,618, filed Jul. 20, 1990, now abandoned.

BACKGROUND OF THE INVENTION

This invention relates to an elastic knee joint bandage in a tubular form with an elastic profile insert encircling the knee cap in an opening.

Similar knee joint bandages are disclosed by German Patent 3,412,772. This bandage includes a profile insert partly encircling the knee joint on both sides with extension flaps. Reinforcements are incorporated in the extension flaps. These reinforcements are used to exert radial pressure on the knee joint from both sides. In another embodiment described in the publication, the profile insert is provided with a toroidal elevation near the opening for the knee cap which also increases the pressure on the knee at its position. As stated in the associated description, this is intended to make it possible to move the knee cap both inward and toward the outside of the knee. Therefore, a static action of the pressure exerted by the elevation on the knee is utilized.

An elastic knee joint bandage is also described in U.S. Pat. No. 4,445,505 that has an opening for the knee cap and in which pads are disposed in a position so as to prevent lateral shifting of the knee cap. To intensify the action of these pads, the knee joint bandage is provided with elastic bands that can be stretched around the bandage by means of conventional fabric-based hook and eye closures, which hold the pads in place. Therefore, this knee joint bandage also involves acting on the knee cap position by exerting static pressure.

SUMMARY OF THE INVENTION

The purpose of this invention is to provide a bandage that acts dynamically on a knee cap that has moved laterally to the side of the fibular and out of its ideal position either pathologically or as a very frequent variant from the norm, and thereby to correct the position of the knee cap. This is accomplished pursuant to the invention by connecting the areas of the profile insert adjacent to the poles of the knee cap by a flexible, unstretchable tension member placed in the curve around the knee cap on the side of the fibula in the profile insert in such a way that when the distance between these areas increases as the knee joint is flexed, the distance of the curve from the line joining the poles of the knee cap is reduced and the edge of the opening of the profile insert on the adjacent side of the knee cap presses it medially with a shifting and centering action.

When the knee joint is flexed, this knee joint bandage is stretched considerably on the front over the knee cap. This stretching is transferred to the profile insert, which is an integral part of the knee joint bandage, so that the areas of the profile insert that are adjacent to the poles of the knee cap are moved away from one another compared to the extended position of the knee joint. Because of this enlargement of distance, traction is exerted on the ends of the tension member so that its central area is drawn to the side of the knee cap. The edge of the opening in the profile insert containing the tension member thereby exerts lateral pressure on the knee cap, which is thus drawn increasingly to the knee cap with the flexing of the knee. This results in a dynamic process in which motion of the knee cap that is otherwise possible without the bandage of the invention is counteracted to the same extent as the tendency toward improper motion of the knee cap. Specifically, the more the knee joint is flexed to an angle of about 90°, the greater is the tendency toward improper shifting, which is counteracted fully by the tension member because of correspondingly increasing lateral pressure on the knee cap.

Since the knee cap never usually shifts toward the inside functionally or anatomically with a stressed femoral musculature, but rather only toward the outside, the only meaningful correction addresses the knee cap slipping toward the outside and produces a central positioning of the knee cap. In motion, the lateral pressure exerted by the tension member, which acts on the knee cap through a layer of soft tissue, when using the bandage pursuant to the invention, will not apply a force by which the position of the knee cap is shifted toward the inside beyond the ideal position, since the position of the tension member and the stretching of the profile insert when the knee is flexed are not sufficient to do this.

The tension member is advantageously incorporated in the profile insert that is permanently connected to it as an unstretchable, flexible cord directly next to the knee cap edge of the profile insert, encircling the knee cap at least from the upper to the lower pole of the knee cap. Because of this position of the cord, it functions to exert a direct effect on the knee cap.

To connect the cord solidly to the profile insert, its ends can be formed into anchors in the material of the profile insert which lie on the side of the joining line between the poles of the knee cap facing away from the curve of the cord. These anchors can advantageously be designed as loops, but it is also possible to provide enlargements of the cord as anchors.

Another possibility for providing a solid connection of the cord to the profile insert includes providing the cord with recesses along its length that are filled with the material of the profile insert. In this case, penetration of the material of the profile insert into the recesses, for example holes in an unstretchable plastic tape, provides that when the profile insert is stretched over the flexed knee, each point along the tension member remains solidly connected to the encircled material of the profile insert.

DESCRIPTION OF THE PREFERRED EMBODIMENT

Figure 1:
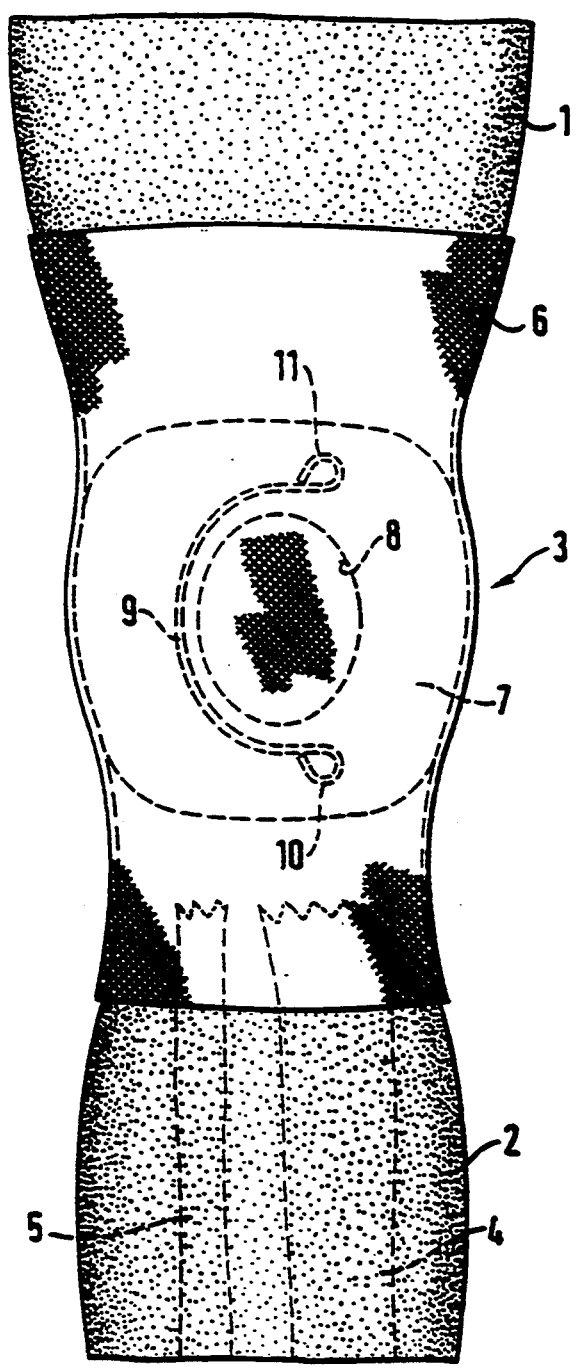
FIG. 1 is a section of a human leg surrounding the knee joint in extended position, with knee joint bandage drawn over the knee joint, with the knee cap in top view.
Figure 3:
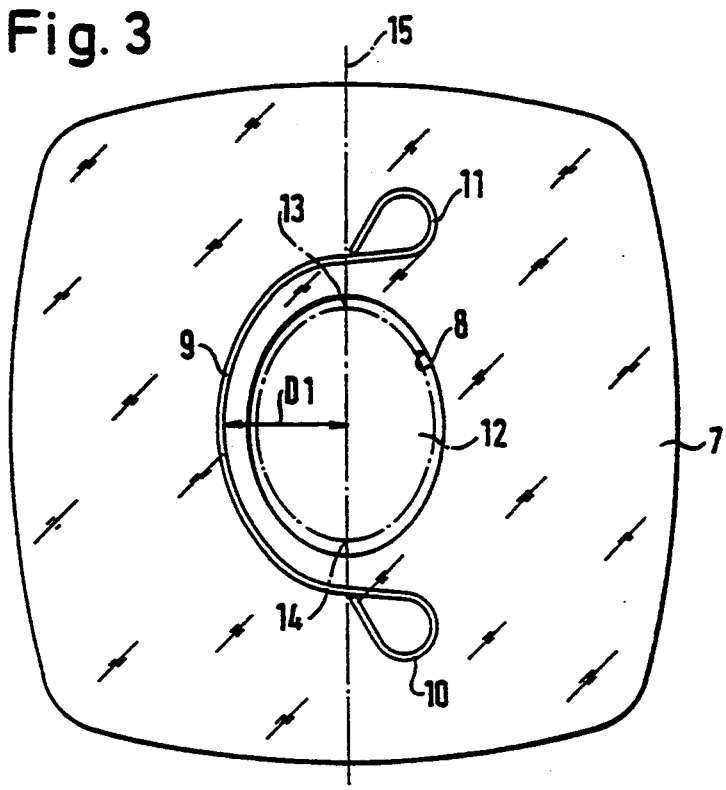
FIG. 3 is a view of the profile insert integrated into the knee joint bandage spread out flat, based on the extended position of the knee.
Figure 4:
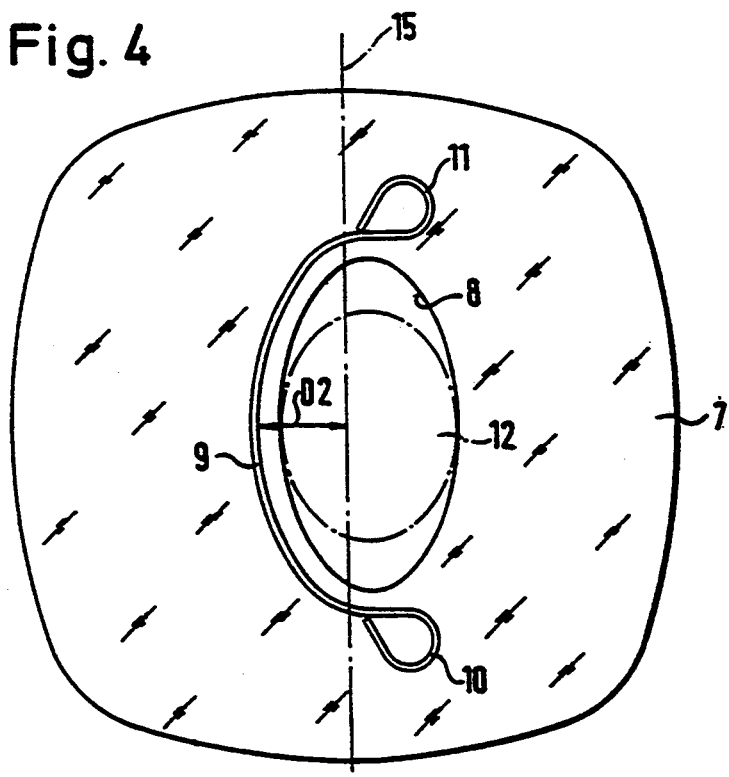
FIG. 4 is a view of the profile insert spread out flat, based on the flexed knee.

FIG. 1 shows the thigh 1 and the lower leg 2 as well as the knee joint 3 of a human leg, with the tibia 4 and the fibula 5 indicated in the lower leg 2. The knee joint bandage 6 consisting of a flexible textile is drawn over the knee joint and is placed tightly around the knee joint 3 and the areas of the thigh 1 that are involved. The profile insert 7, described in further detail with reference to FIGS. 3 and 4, is incorporated in the knee joint bandage 6, and forms a pad consisting of elastic material. Silicone rubber can be used as the material for this, for example, in a known way. The profile insert 7 is provided with the opening 8 in the area of the knee cap, not shown here, which closely encircles the knee cap. The cord 9 that acts as a tension member is incorporated in the profile insert 7, and can be designed, for example, as a wire cable. The cord is thus flexible but unstretchable, so that it is able to follow deformations of the profile insert 7 without lengthening. The cord 9 is provided with the loops 10 and 11 at its ends that provide secure anchoring of the cord 9 in the profile insert 7, which is discussed in detail in connection with FIGS. 3 and 4.

The profile insert 7 is advantageously incorporated in the knee Joint bandage 6 during its production, but it is also possible to cement or weld the profile insert to the bandage. In any case, the profile insert 7 is an integral part of the knee joint bandage 6 in the sense that when the knee 3 is flexed, both the knee joint bandage 6 and the profile insert 7 take part in the motion, without the possibility of shifting between the knee joint bandage 6 and the profile insert 7.

Figure 2:
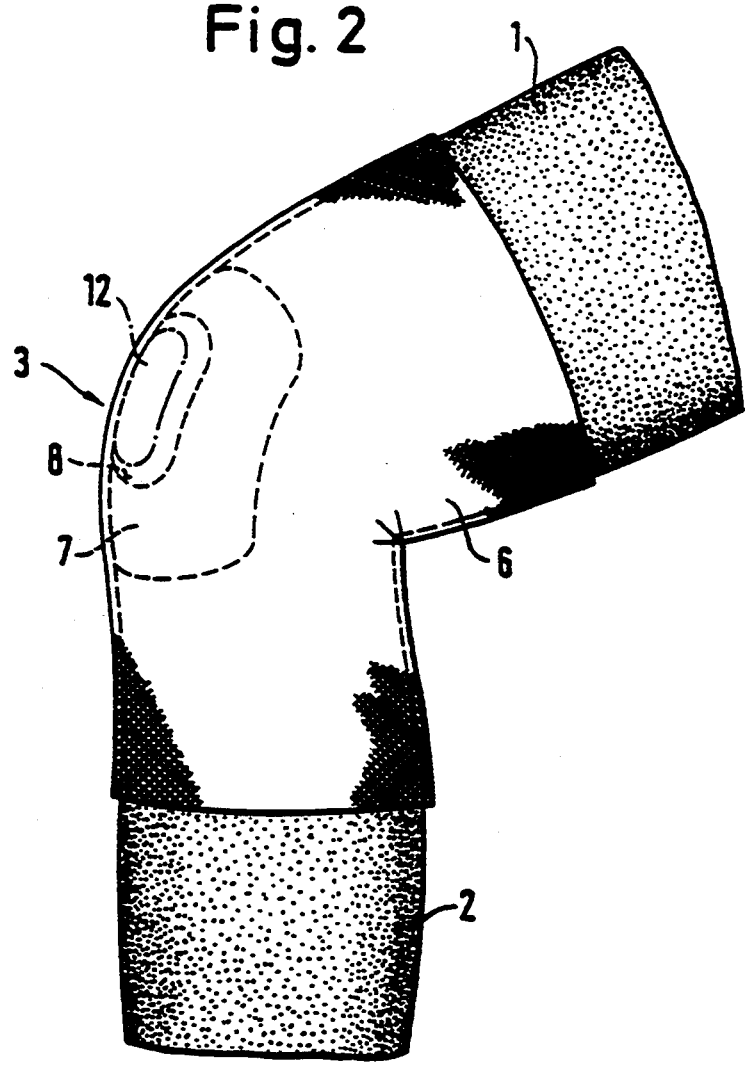
FIG. 2 is the leg viewed from the side in a flexed position with a knee joint bandage drawn over it.

FIG. 2 shows the same knee joint bandage 6 with the profile insert 7 contained in it and the knee 3 flexed. In FIG. 2, the knee cap 12 is indicated in the area of the opening 8 of the profile insert 7 by dots and dashes.

FIGS. 3 and 4 show the profile insert 7 spread out flat, with the knee extended in FIG. 3 (see FIG. 1), and with the knee flexed in FIG. 4 (see FIG. 2). Furthermore, the knee cap 12 is also shown in FIGS. 3 and 4 by dots and dashes.

The profile insert 7 of FIG. 3 contains the cord 9 with the two loops 10 and 11 serving as anchors. In FIG. 3, the centerline 15 running through the poles 13 and 14 of the knee cap 12 is shown, which maintains the distance D1 from the curve of the cord 9. This curve loops around the knee cap 12 within the material of the profile insert 7 on the side of the fibula 5 (in FIG. 1) and it then runs beyond the centerline 15, where the cord 9, as stated above, then forms the loops 10 and 11. The position of the knee cap 12 and the profile insert 7 shown in FIG. 3 represents the normal position of the knee cap 12 of the patient in question—but already slightly on the outside of the ideal position as a variant from the norm—together with the profile insert 7 encircling the knee cap 12.

When the knee joint 3 encircled by the knee joint bandage 6 pursuant to the invention is then flexed (see FIG. 2), stretching occurs for the knee joint bandage 6 and the profile insert 7 anchored in it on the outside of the knee joint 3, which leads to the opening 8 being stretched along the centerline 15, whereby it assumes an approximately oval shape. This is shown in FIG. 4, with the profile insert 7 of course being drawn spread out flat. Since the cord 9 consists of unstretchable material and it is anchored solidly in the material of the profile insert 7, the areas of the cord 9 in front of loops 10 and 11 are drawn apart from one another along the centerline 15, which results in the cord being drawn toward the centerline 15 in its curved area because it cannot be stretched. The distance of the curved area of the cord 9 from the centerline 15 is thus reduced to the length D2. The profile insert 7 together with the knee joint bandage 6 is retained in position in principle because of the solid encirclement of the knee joint 3, so that the reduction of the distance between the curved area of the cord 9 and the centerline 15 from the length D1 to the length D2 has the effect that the edge 19 of the opening 8 presses against the edge of the knee cap 12 from its side and shifts it toward the inside of the leg. The degree of this shift depends on the angle of flexion of the knee joint 3.

Proceeding from the position of the knee cap 12 illustrated in FIG. 3, which corresponds to an improper position, a correction into the ideal position is thus obtained because of the lateral shifting of the knee cap 12 shown in FIG. 4, with a shift of a few millimeters being involved, which FIG. 4 shows inasmuch as it shows the conditions on a scale of about 1:1.

This change of position of the knee cap 12 of only a few millimeters provides medically a substantial improvement of the pressure conditions in the knee cap-femoral joint, on the other hand, since the inner surface of the knee cap is now in ideal congruence relative to the femoral joint surface in motion.

Figure 5:
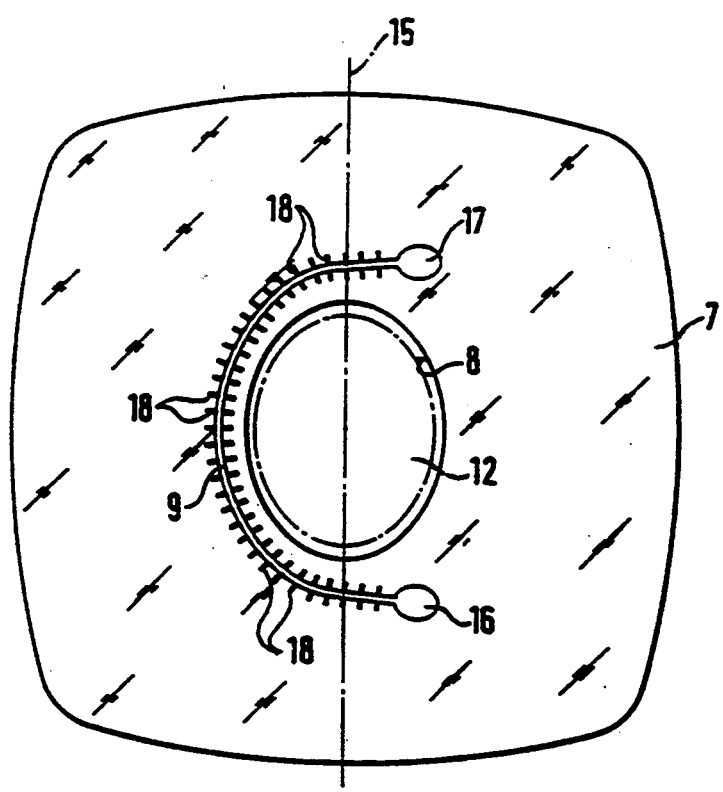
FIG. 5 is a view of the profile insert spread out flat with enlargements as anchors of the cord.

FIG. 5 illustrates a variant of the method of anchoring the cord 9 in the profile insert 7. This involves the two enlargements 16 and 17 at the ends of the cord 9, which in this case consists of a flexible, unstretchable plastic strand. It is also shown that the cord 9 is provided with a number of spreaders 18 along its length, with which the cord 9 penetrates into the material of the profile insert 7 and thus provides for additional anchoring, which may be adequate by itself. It should be also pointed out that the anchoring of the cord 9 along its length, for example, can also be accomplished by providing the cord with recesses, for example in the form of holes, which are then filled by the material of the profile inserts 7. In this case, a ladder-like perforated plastic tape is suitable for use as the cord.

While it is apparent that modifications and changes may be made within the spirit and scope of the present invention, it is our intention, however, only to be limited by the scope of the appended claims.

As our invention, we claim:

1. Elastic knee-joint bandage (6) in tubular form with an elastic profile insert (7) encircling the knee cap (12) in an opening (8), characterized by the fact that a flexible, non-stretchable tension member (9) is wholly and fixedly embedded as an integral part of the profile insert (7) in permanent connection to it, said tension member (9) connecting the areas of the profile insert (7) adjacent to the poles (13, 14) of the knee cap (12) in a curve around the knee cap (12) on the side of the fibula (5) in such a way that when the distance between these areas is increased by flexing the knee joint (3) the distance of the curve from the line joining the poles (13, 14) of the knee cap is reduced and the edge of the opening (8) of the profile insert (7) on the adjacent of the knee cap (12) presses the knee cap (12) medially with a shifting and centering effect.

2. Knee-joint bandage pursuant to claim 1 characterized by the fact that the tension member is an unstretchable, flexible cord (9) disposed directly next to the edge of the profile insert (7) on the knee cap side, encircling the knee cap (12) at least from the upper pole to the lower pole of the knee cap (13, 14).

3. Knee-joint bandage pursuant to claim 2, characterized by that the ends of the cord (9) are shaped into anchors (10,11; 16,17) in the material of the profile insert (7), which lie on the side of the joining line between the poles (13,14) of the knee cap facing away from the curve of the cord (9).

4. Knee-joint bandage pursuant to claim 3, characterized by the fact that the anchors are designed as loops (10,11).

5. Knee-cap-joint bandage pursuant to claim 3, characterized by the fact that the anchors are designed as enlargements (16,17) of the cord (9).

6. Knee-joint bandage pursuant to claim 5, characterized by the fact that the cord (9) is provided with recesses, for example holes, along its length, which are filled with the material of the profile insert.

* * * * *